(12) United States Patent
Endo

(10) Patent No.: US 8,136,251 B2
(45) Date of Patent: Mar. 20, 2012

(54) HAND TOOL

(75) Inventor: Masahiro Endo, Seki (JP)

(73) Assignee: Kai R&D Center Co., Ltd., Gifu-ken (JP)

( * ) Notice: Subject to any disclaimer, the term of this patent is extended or adjusted under 35 U.S.C. 154(b) by 478 days.

(21) Appl. No.: 12/309,139

(22) PCT Filed: Jul. 30, 2007

(86) PCT No.: PCT/JP2007/064881
§ 371 (c)(1),
(2), (4) Date: Jan. 8, 2009

(87) PCT Pub. No.: WO2008/029566
PCT Pub. Date: Mar. 13, 2008

(65) Prior Publication Data
US 2009/0204136 A1    Aug. 13, 2009

(30) Foreign Application Priority Data
Sep. 8, 2006    (JP) .................. 2006-243916

(51) Int. Cl.
*B26B 1/08* (2006.01)
*A61B 17/32* (2006.01)
(52) U.S. Cl. .............................. 30/162; 30/335; 606/167
(58) Field of Classification Search .................... 30/151, 30/162, 335; 606/166, 167
See application file for complete search history.

(56) References Cited

U.S. PATENT DOCUMENTS

| | | | |
|---|---|---|---|
| 2,226,324 A | | 12/1940 | Prescott |
| 2,885,779 A | | 5/1959 | Newkirk |
| 3,176,395 A | | 4/1965 | Warner |
| 4,499,898 A | * | 2/1985 | Knepshield et al. .......... 606/166 |
| 5,222,951 A | * | 6/1993 | Abidin et al. ...................... 606/1 |
| 5,330,493 A | * | 7/1994 | Haining ........................ 606/167 |
| 5,391,177 A | * | 2/1995 | Schwartz ...................... 606/167 |
| 5,431,671 A | | 7/1995 | Nallakrishnan |
| 5,475,925 A | * | 12/1995 | Newman et al. ................ 30/162 |
| 5,481,804 A | * | 1/1996 | Platts .............................. 30/162 |

(Continued)

FOREIGN PATENT DOCUMENTS

JP    U-6-55796    8/1994

(Continued)

OTHER PUBLICATIONS

Extended European Search Report dated Sep. 24, 2010 issued in corresponding European patent application No. 07791566.8.

(Continued)

*Primary Examiner* — Hwei C Payer
(74) *Attorney, Agent, or Firm* — Posz Law Group, PLC

(57) ABSTRACT

A hand tool includes a holder and a movable head portion to which a blade body is secured. The movable head portion is supported by the holder in a manner movable relative to the holder between an accommodated state Q, in which the movable head portion is accommodated in the holder together with the blade body, and a projected state, in which the blade body is projected from the holder. The orientation N of the blade body in the accommodated state Q and the orientation N of the blade body in the projected state are different from each other. This improves operation of the blade body both in the accommodated state Q and the projected state and reduces the size of a front opening of the holder to provide a compact holder of the hand tool such as a medical edged tool.

6 Claims, 8 Drawing Sheets

U.S. PATENT DOCUMENTS

| | | | |
|---|---|---|---|
| 5,571,128 A * | 11/1996 | Shapiro | 606/167 |
| 6,022,364 A * | 2/2000 | Flumene et al. | 606/166 |
| 6,530,903 B2 * | 3/2003 | Wang et al. | 604/195 |
| 6,623,499 B1 * | 9/2003 | Andreini et al. | 606/167 |
| 6,948,250 B1 | 9/2005 | Caiafa | |

FOREIGN PATENT DOCUMENTS

| | | |
|---|---|---|
| JP | A-07-047075 | 2/1995 |
| JP | A-11-115377 | 4/1999 |

OTHER PUBLICATIONS

PCT International Search Report mailed on Oct. 30, 2007 for the corresponding international patent application No. PCT/JP2007/064881.

International Preliminary Report on Patentability issued from the International Bureau of WIPO on Mar. 17, 2009 in the corresponding International patent application No. PCT/JP2007/064881.

* cited by examiner

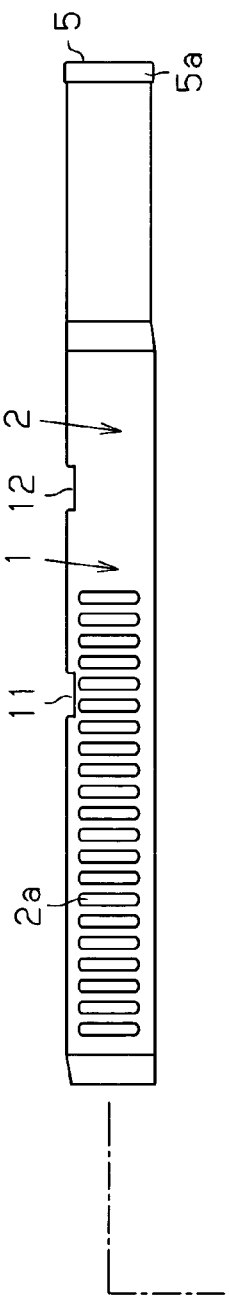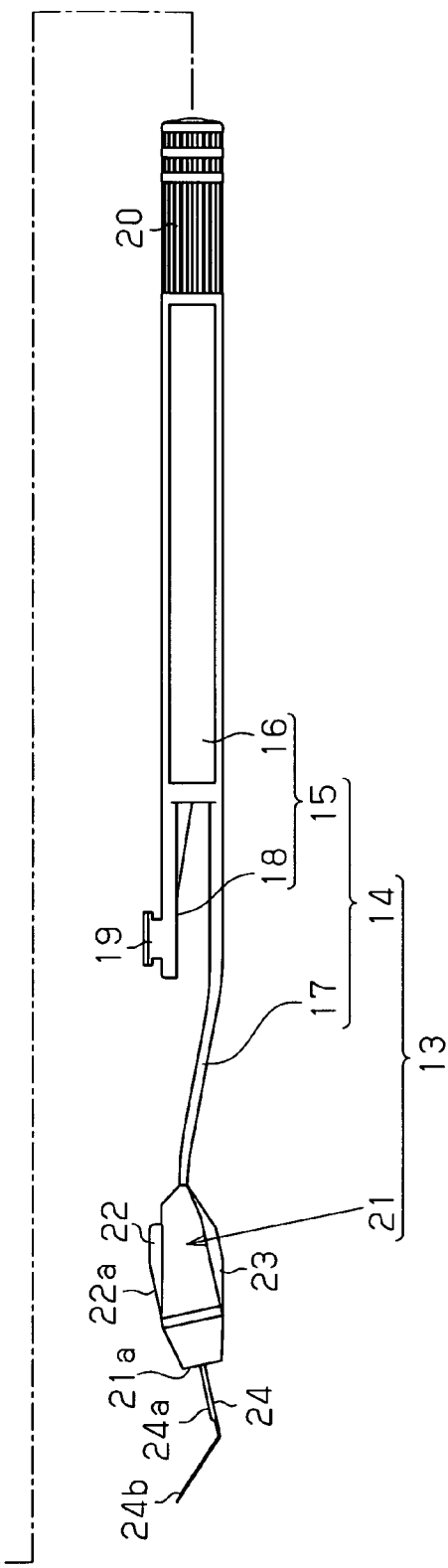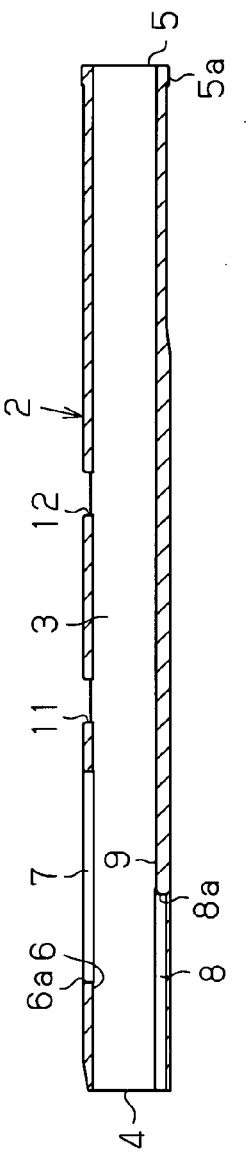

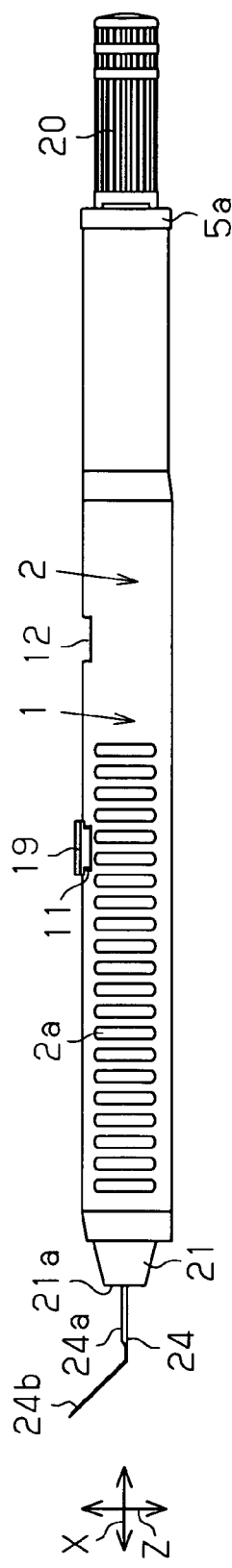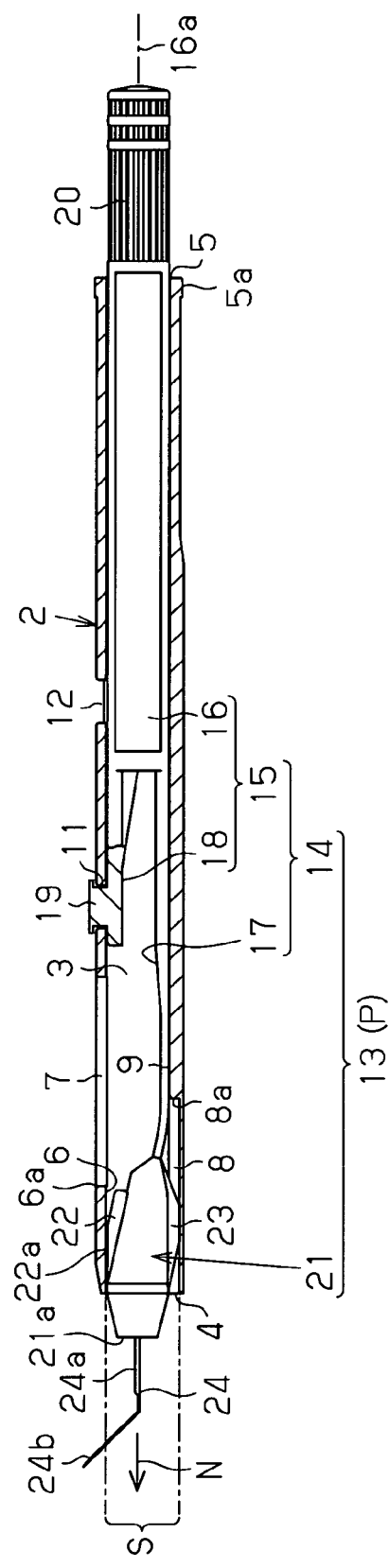

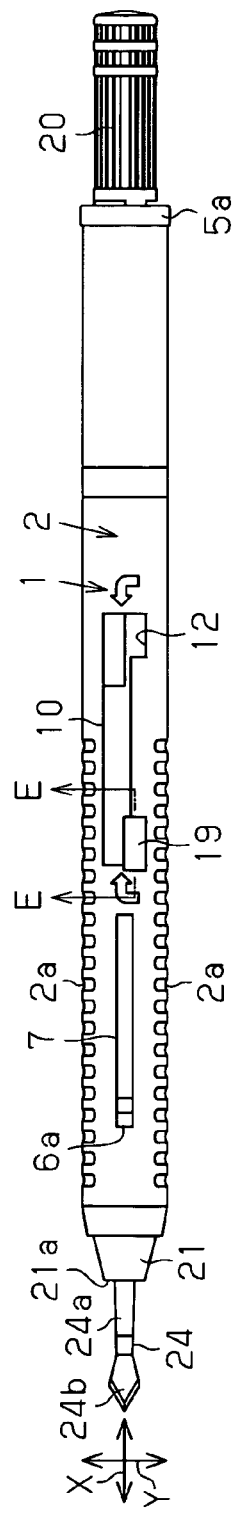
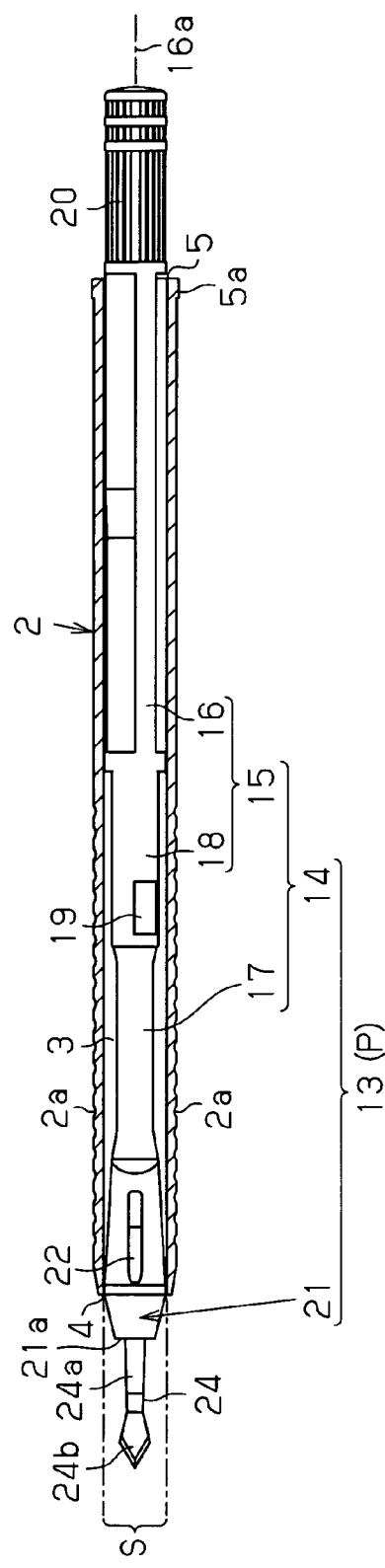

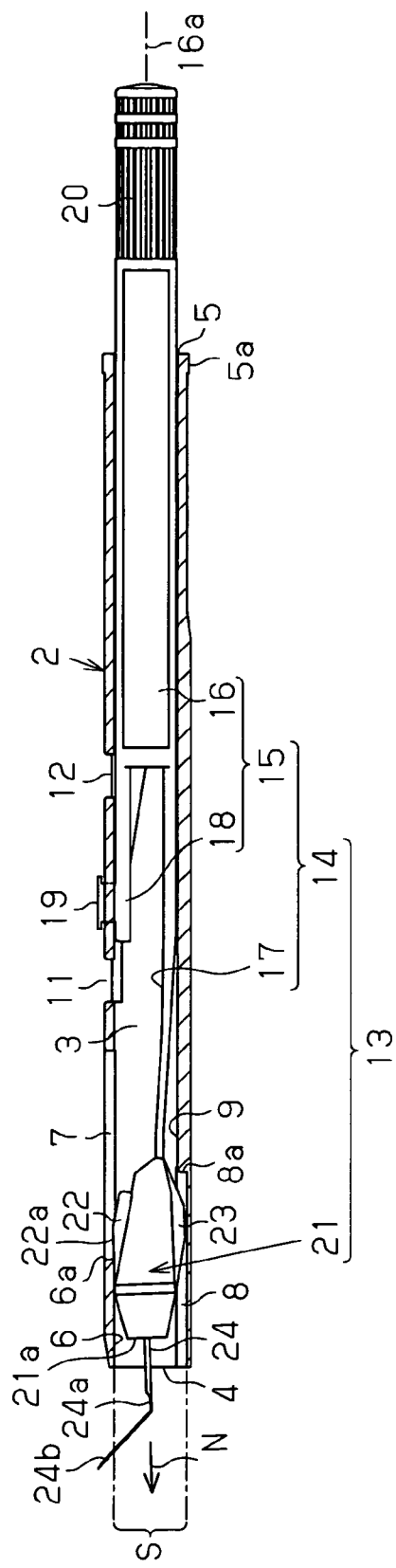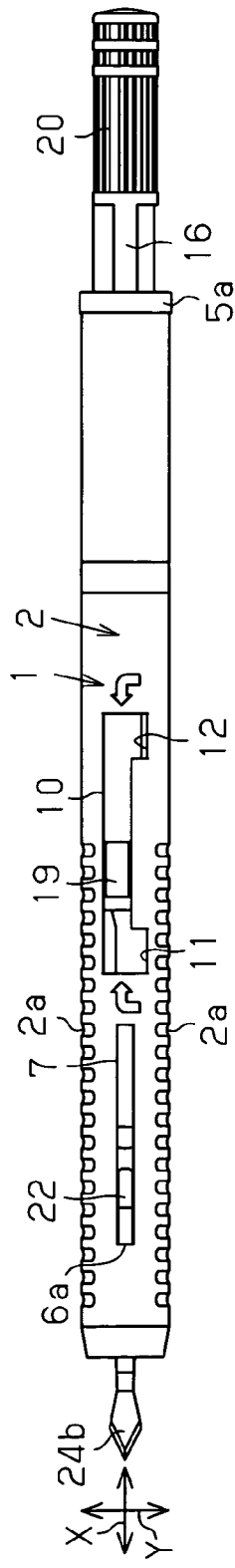

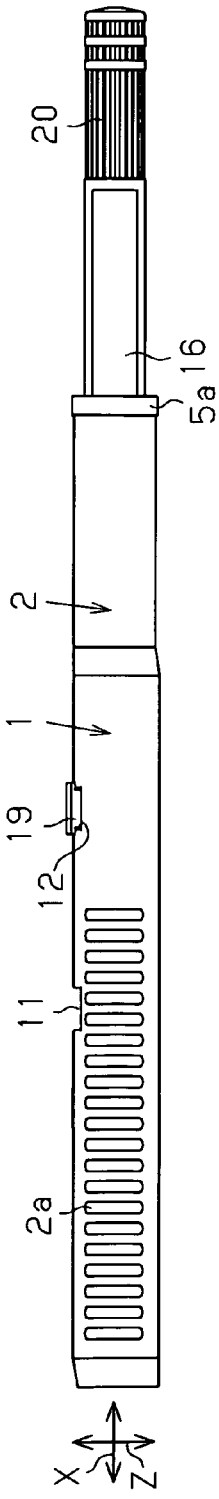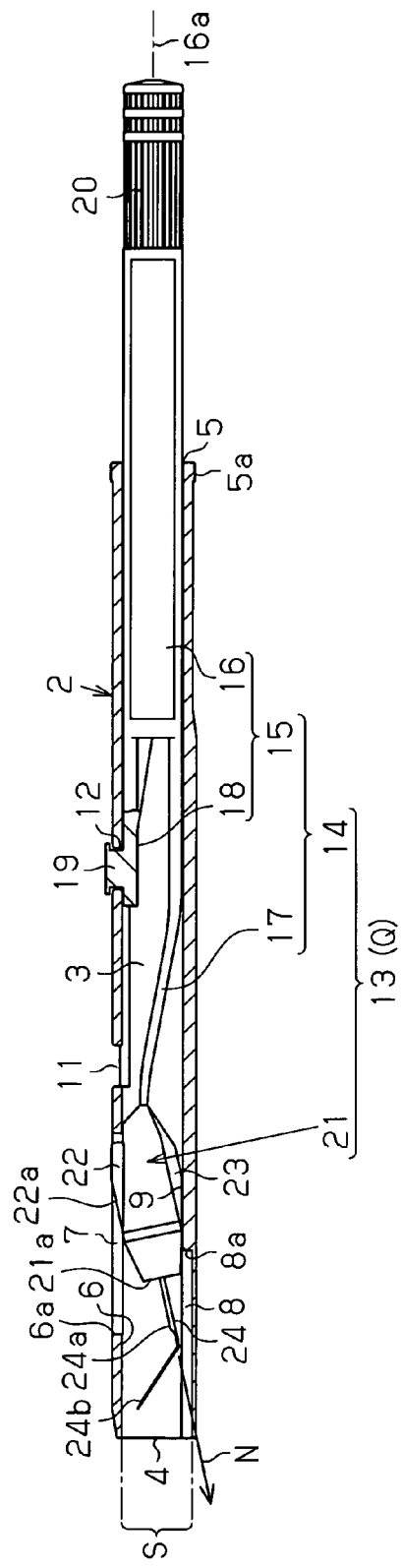

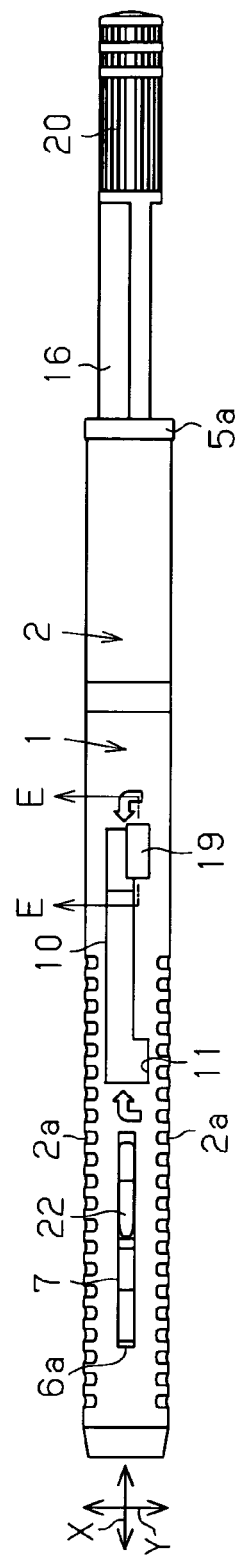
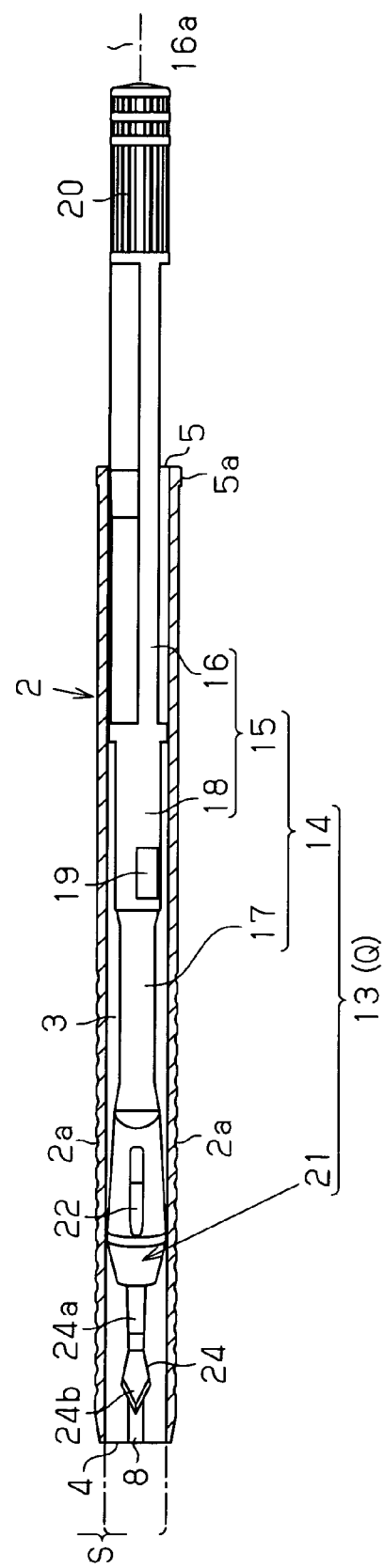

HAND TOOL

CROSS REFERENCE TO RELATED APPLICATIONS

This application is a U.S. national stage application of PCT/JP2007/064881 filed on Jul. 30, 2007, and claims priority to, and incorporates by reference, Japanese Patent Application No. 2006-0243916 filed on Sep. 8, 2006.

FIELD OF THE INVENTION

The present invention relates to a hand tool, or, for example, a medical edged tool, having an accommodated state, in which a functional portion such as a blade body is accommodated in a holder, and a projected state, in which the functional portion projects from the holder.

BACKGROUND OF THE INVENTION

Conventionally, a hand tool, which is, for example, a medical edged tool, includes a functional portion such as a blade body and a holder in which the functional portion is accommodated. The functional portion is bent and moves relative to the holder in such a manner that the hand tool is switched between an accommodated state and a projected state of the functional portion (see, for example, Patent Document 1).
Patent Document 1: Japanese Laid-Open Patent Publication No. 7-47075

SUMMARY OF THE INVENTION

However, if the functional portion such as the blade body is bent but an inlet opening of the holder is not sized sufficiently large for the functional portion, the functional portion cannot be accommodated in the holder. As a result, the conventional hand tool disadvantageously has a holder with a large-sized inlet opening, which, in turn, increases the size of the holder as a whole.

Accordingly, it is an objective of the present invention to reduce the size of an inlet opening of a holder of a hand tool such as a medical edged tool by improving operation of a functional portion both in an accommodated state and a projected state.

In order to achieve the foregoing objective and in accordance with a first aspect of the present invention, a hand tool having a holder and a movable head portion to which a functional portion is secured is provided. The movable head portion is supported by the holder in a manner movable relative to the holder between an accommodated state, in which the movable head portion is accommodated in the holder together with the functional portion, and a projected state, in which the functional portion is projected from the holder. The orientation of the functional portion in the accommodated state and the orientation of the functional portion in the projected state are different from each other. This structure is suitable particularly for a hand tool having a bendable functional portion. Specifically, the orientation of the functional portion is changed so that the functional portion is switched from the projected state, which facilitates use of the functional portion, to the accommodated state, which facilitates accommodation of the functional portion. This reduces the size of the inlet opening of the holder, which accommodates the functional portion.

In the above described configuration, it is preferable that the movable head portion incline when moving relative to the holder between the accommodated state and the projected state. As a result, the functional portion is easily projected from and retracted into the inlet opening of the holder.

In the above configuration, it is preferable that the hand tool further include a manipulation body that supports the movable head portion, and that the manipulation body allow the movable head portion to move between the accommodated state and the projected state. As a result, the movable head portion is easily moved between the accommodated state and the projected state.

In the above configuration, it is preferable that the manipulation body include an elastic body that applies an elastic force to the movable head portion between the accommodated state and the projected state, and that the elastic body cause the movable head portion to incline. As a result, the movable head portion is easily inclined between the accommodated state and the projected state by means of the elastic body.

In the above configuration, it is preferable that the holder and the movable head portion include a guiding/restricting portion that guides the movable head portion in a manner movable relative to the holder between the accommodated state and the projected state and allows the movable head portion to incline. As a result, the movable head portion is smoothly inclined by means of the guide and restricting portion.

In the above configuration, it is preferable that the movable head portion be accommodated in the holder by the elastic force of the elastic body, and that the movable head portion project the functional portion from the holder against the elastic force of the elastic body. As a result, the movable head portion is further easily inclined between the accommodated state and the projected state by means of the elastic body.

In the above configuration, it is preferable that the manipulation body further include a manipulating portion having a finger support portion, and that the elastic body be arranged between the manipulating portion and the movable head portion, and wherein the movable head portion is supported by the elastic body. As a result, the elastic body that urges the movable head portion becomes compact with respect to the manipulation body.

In the above configuration, it is preferable that the manipulating portion and the elastic body of the manipulation body be formed integrally with the movable head portion. As a result, the manipulation body and the movable head portion are easily provided.

In the above configuration, it is preferable that the guiding/restricting portion of the movable head portion be a guide projection, and that the guiding/restricting portion of the holder include a pressing portion that presses and contacts the guide projection of the movable head portion and an escape portion that releases the guide projection from pressing and contacting. This simplifies the configuration of each guiding/restricting portion.

In accordance with a second aspect of the present invention, a hand tool having a holder and a movable head portion to which a functional portion is secured is provided. The movable head portion is supported by the holder in a manner movable relative to the holder between an accommodated state, in which the movable head portion is accommodated in the holder together with the functional portion, and a projected state, in which the functional portion is projected from the holder. The position of the functional portion in the accommodated state and the position of the functional portion in the projected state are different in a longitudinal direction of the holder and in a direction perpendicular to the longitudinal direction. This structure is suitable particularly for a hand tool having a bendable functional portion. Specifically, the position of the functional portion is changed so that the functional portion is switched from the projected state, which facilitates use of the functional portion, to the accommodated state, which facilitates accommodation of the functional portion. This reduces the size of the inlet opening of the holder in which the functional portion is accommodated.

BRIEF DESCRIPTION OF THE DRAWINGS

FIG. 1(a) is an exploded side view showing a medical edged tool according to one embodiment of the present invention, with a core member removed from the holder;

FIG. 1(b) is a cross-sectional side view showing the holder;

FIG. 2(a) is a side view illustrating a blade body in a projected state;

FIG. 2(b) is a partial cross-sectional view showing the blade body in the state of FIG. 2(a);

FIG. 3(a) is a plan view showing the blade body in a projected state;

FIG. 3(b) is a partial cross-sectional view showing the blade body in the state of FIG. 3(a);

FIG. 4(a) is a partial cross-sectional view showing the blade body in a transitional state between the projected state and the accommodated state;

FIG. 4(b) is a plan view showing the blade body in the state of FIG. 4(a);

FIG. 5(a) is a side view showing the blade body in the accommodated state;

FIG. 5(b) is a partial cross-sectional view showing the blade body in the state of FIG. 5(a);

FIG. 6(a) is a side view showing the blade body in the accommodated state;

FIG. 6(b) is a partial cross-sectional view showing the blade body in the state of FIG. 6(a);

DETAILED DESCRIPTION OF THE INVENTION

Figure 7A:
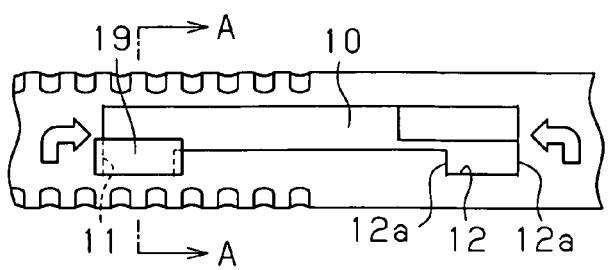
FIG. 7(a) is a plan view showing a portion of FIG. 3(a) held in a locked state.

A hand tool according to one embodiment of the present invention will now be described with reference to the attached drawings. The hand tool of the embodiment is a medical edged tool. As shown in FIGS. 1(a) to 6(b), a holder 1 of the medical edged tool includes an outer circumferential wall 2 having an elongated cylindrical shape extending along the longitudinal direction X of the holder 1. An inner bore 3, which is provided in the space surrounded by the outer circumferential wall 2, is open at a front opening 4, or an inlet opening at the front end of the holder 1, and a rear opening 5, which is provided at the rear end of the holder 1.

A pressing portion 6, or a guiding/restricting portion, is provided in an upper portion of the outer circumferential wall 2 in the up-and-down direction Z of FIG. 2(a) and extends rearward from the front opening 4. A pressing escape hole 7, or an escape portion formed continuously from the pressing portion 6 through a step 6a, is formed in the upper portion of the outer circumferential wall 2 and extends rearward. The inner bore 3 is exposed to the exterior through the pressing escape hole 7. A guide groove 8, or an escape portion, is provided in a lower portion of the outer circumferential wall 2 in the up-and-down direction Z of FIG. 2(a) and extends rearward from the front opening 4. The guide groove 8 faces the pressing portion 6 and the pressing escape hole 7. A receiving portion 9, which is formed continuously from the guide groove 8 through a step 8a, is provided in the lower portion of the outer circumferential wall 2 and extends rearward. The receiving portion 9 faces the pressing escape hole 7.

A guide hole 10 extends along the longitudinal direction X at a position slightly rearward from the pressing escape hole 7 in the upper portion of the outer circumferential wall 2. Engagement recesses 11, 12, or engagement portions extending in the circumferential direction R of the holder 1, are provided at a front end portion and a rear end portion of the guide hole 10. Specifically, the engagement recess 11 is provided at the front end portion of the guide hole 10 and the engagement recess 12 is formed at the rear end portion of the guide hole 10. As illustrated in FIGS. 7(a) to 10(b), end portions 11a and end portions 12a, each serving as a stopper portion, are formed at both front and rear end portions of the engagement recess 11 and the engagement recess 12, respectively. The holder 1 is formed of polycarbonate resin by injection molding. The components forming the holder 1 are molded as an integral body and the holder 1 is transparent.

Figure 11:
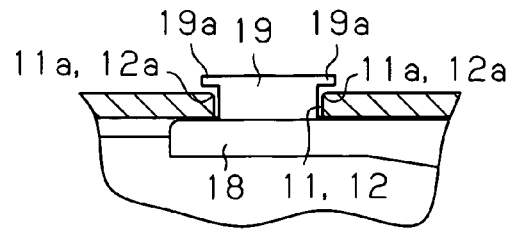
FIG. 11(a) is a cross-sectional view taken along line E-E of either FIG. 3(a) or FIG. 6(a)
FIGS. 11(b), 11(c), and 11(d) are diagrams corresponding to FIG. 11(a), each showing an engagement projection and an engagement recess of a modification.
Figure 11:
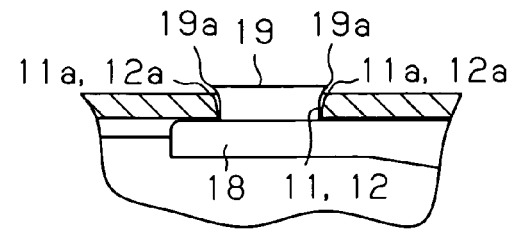
Figure 11:
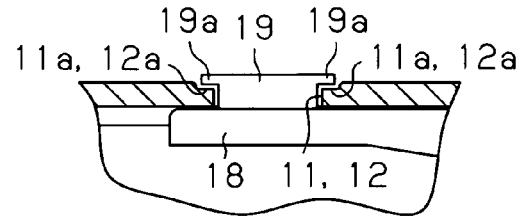
Figure 11:
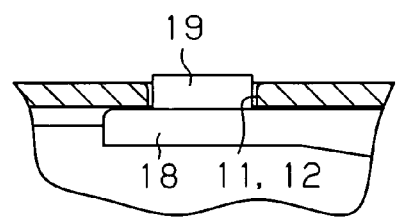

A core member 13 of the medical edged tool includes a manipulation body 14 and a movable head portion 21. The manipulation body 14 has a manipulating portion 15 formed mainly by a movable rod 16 and a leaf spring portion 17 serving as an elastic body extending forward from a lower portion of the front end of the movable rod 16. A base plate 18 having a cantilevered shape extends forward from an upper portion of the front end of the movable rod 16. An engagement projection 19 projects from the base plate 18. With reference to FIG. 11(a), a brim 19a serving as a stopper portion projects from each one of a front end portion and a rear end portion of the engagement projection 19. A finger support portion 20 is formed at a rear end portion of the movable rod 16.

A proximal portion of the movable head portion 21 is supported by a distal portion of the leaf spring portion 17 at a position forward from the engagement projection 19 on the base plate 18. Guide projections 22, 23 project from both upper and lower end portions of the movable head portion 21. Specifically, the guide projection 22 is formed on the upper end portion of the movable head portion 21 and the guide projection 23 is provided at the lower end portion of the movable head portion 21. The guide projections 22, 23, the pressing portion 6, the pressing escape hole 7, the guide groove 8, and the receiving portion 9 form a guiding/restricting portion. A blade body 24, or a functional portion, is secured to a distal surface 21a of the movable head portion 21. The blade body 24 has a support plate portion 24a extending forward from the distal surface 21a of the movable head portion 21 and a blade plate portion 24b extending diagonally upward from a distal portion of the support plate portion 24a. The blade body 24 is formed of stainless steel. The core member 13, which is configured by the movable head portion 21 and the manipulation body 14, is formed of polybutadiene terephthalate resin. The components forming the core member 13, except for the blade body 24, are molded as an integral body.

To insert the core member 13 into the holder 1 and engage the core member 13 with the holder 1, the finger support portion 20 of the movable rod 16 is inserted into the holder 1 from the front opening 4 of the holder 1 and thus projected from the rear opening 5. At this stage, the base plate 18 flexibly deforms in the up-and-down direction Z against the elastic force of the base plate 18. The engagement projection 19 on the base plate 18 is thus allowed to move along the inner circumference of the outer circumferential wall 2 and engaged with the guide hole 10. The finger support portion 20 is always exposed from the rear opening 5 located at a position opposite to the front opening 4 from which the movable head portion 21 is selectively projected from and retracted into the holder 1. On the outer circumferential surface of the outer circumferential wall 2, the arrows illustrated at positions in front of and at the rear of the guide hole 10, each represent a movement direction of the engagement projection 19 when the engagement projection 19 is operated.

Figure 7B:
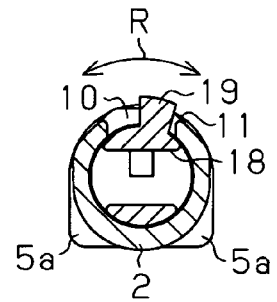
FIG. 7(b) is a cross-sectional view taken along line A-A of FIG. 7(a)

In a projected state P, as illustrated in FIGS. 2(a) to 3(b), in which a front portion of the movable head portion 21 and the blade body 24 project outward from the front opening 4 of the holder 1, the engagement projection 19 is located in the engagement recess 11 and thus prevented from moving in the longitudinal direction X, as illustrated in FIGS. 7(a) and 7(b). In this state, the engagement projection 19 is engaged with the engagement recess 11. This locks the core member 13 in the projected state P. In this state, with reference to FIG. 11(a), the brims 19a of the engagement projection 19 contact the end portions 11a of the engagement recess 11 despite the fact that the base plate 18 is flexibly deformed and received in the holder 1. This prevents the engagement projection 19 from entering the holder 1. In the movable head portion 21, the guide projection 22, or particularly an inclined surface 22a of the guide projection 22, is pressed downward by the pressing portion 6 against the elastic force of the leaf spring portion 17. The distal surface 21a thus becomes inclined upward and the guide projection 23 is received in the guide groove 8. The guide projection 23 is thus prevented from pivoting in the circumferential direction R about the axis 16a of the movable rod 16. In this state, the guide projection 23 is engaged with the guide groove 8. Further, the outer circumferential surface of a portion of the movable head portion 21 located slightly forward from the guide projections 22, 23 contacts the inner circumferential surface of the outer circumferential wall 2 including the pressing portion 6. This stops the movable head portion 21 from moving in the up-and-down direction Z or the left-and-right direction Y, thus stably maintaining the movable head portion 21 in the projected state P.

Figure 8A:
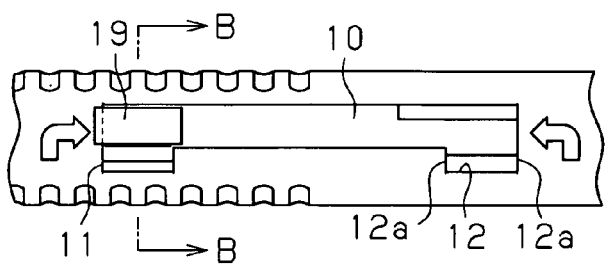
FIG. 8(a) is a plan view showing a portion of FIG. 3(a) held in an unlocked state.
Figure 8B:
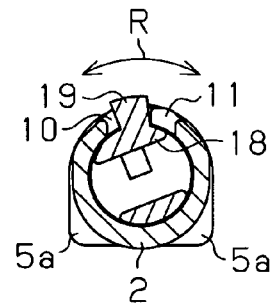
FIG. 8(b) is a cross-sectional view taken along line B-B of FIG. 8(a)

In the projected state P, the finger support portion 20 is gripped and the movable rod 16 is twisted relative to the holder 1 in the circumferential direction R about the axis 16a of the movable rod 16 against the elastic force of the leaf spring portion 17. In this state, with the movable head portion 21 fixed without rotating relative to the holder 1, the engagement projection 19 is released from the engagement recess 11 and received in the guide hole 10, as illustrated in FIGS. 8(a) and 8(b). This unlocks the core member 13 from the projected state P. Anti-slip serrations are formed on the outer circumference of the finger support portion 20, thus allowing the movable rod 16 to be easily twisted.

Figure 9A:
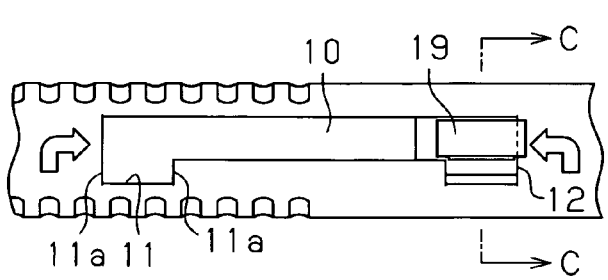
FIG. 9(a) is a plan view showing a portion of FIG. 6(a) held in the unlocked state.
Figure 9B:
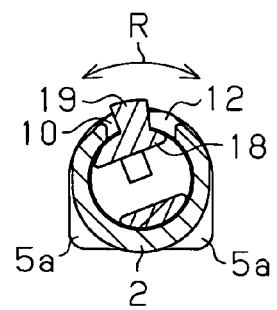
FIG. 9(b) is a cross-sectional view taken along line C-C of FIG. 9(a)
Figure 10A:
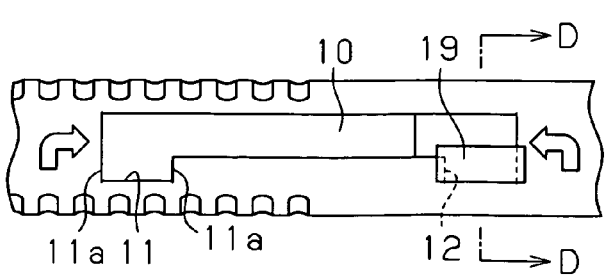
FIG. 10(a) is a plan view showing a portion of FIG. 6(a) held in the locked state.
Figure 10B:
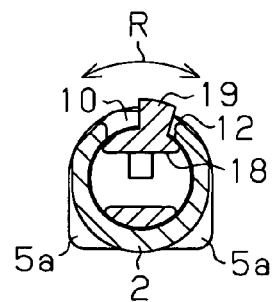
FIG. 10(b) is a cross-sectional view taken along line D-D of FIG. 10(a)

As illustrated in FIGS. 4(a) and 4(b), the movable rod 16 is pulled rearward while twisted with the finger support portion 20 held in a gripped state. In this state, the engagement projection 19 is moved along the guide hole 10 and sent to a position adjacent to the engagement recess 12, as viewed in FIGS. 9(a) and 9(b). In such movement of the engagement projection 19, the guide projection 22 of the movable head portion 21 is released from the pressing portion 6 and received in the pressing escape hole 7, as illustrated in FIGS. 5(a) to 6(b). Meanwhile, the guide projection 23 is disengaged from the guide groove 8 and supported by the receiving portion 9. In this state, the guide projection 22 is engaged with the pressing escape hole 7. Then, the elastic force of the leaf spring portion 17 causes the leaf spring portion 17 to restore its upper position so that the distal surface 21a becomes inclined downward. If the engagement projection 19 is arranged in the guide hole 10, the guide hole 10 receives the twisting force of the movable rod 16. After the movable rod 16 is released from gripping and the movable head portion 21 becomes fixed without rotating relative to the holder 1, as illustrated in FIGS. 10(a) and 10(b), the elastic force of the leaf spring portion 17 causes the movable rod 16 to restore its original position, canceling the twisting force of the movable rod 16. Further, the engagement projection 19 automatically enters the engagement recess 12 and is thus prevented from moving in the longitudinal direction X. This locks the core member 13 in an accommodated state Q. In this state, the engagement projection 19 is engaged with the engagement recess 12.

When shifting from the projected state P to the accommodated state Q, the movable head portion 21 and the blade body 24 become inclined so that the orientations N of the movable head portion 21 and the blade body 24 are changed by approximately 12 degrees as illustrated in FIGS. 2(b), 4(a), and 5(b). In other words, in the projected state P, the blade plate portion 24b of the blade body 24 is projected outside of the range S defined by extending the front opening 4 of the holder 1 in the longitudinal direction X. In the accommodated state Q, the movable head portion 21 and the blade body 24 are inclined downward and held within the range S.

In the accommodated state Q, the finger support portion 20 is gripped and the movable rod 16 is twisted relative to the holder 1 in the circumferential direction R about the axis 16a of the movable rod 16 against the elastic force of the leaf spring portion 17. In this state, while the movable head portion 21 is maintained fixed without rotating relative to the holder 1, the engagement projection 19 is disengaged from the engagement recess 12 and received in the guide hole 10 as illustrated in FIGS. 9(a) and 9(b). This unlocks the core member 13 from the accommodated state Q.

With reference to FIGS. 4(a) and 4(b), the movable rod 16 is pressed forward while held in a twisted state with the finger support portion 20 gripped. This moves the engagement projection 19 along the guide hole 10 and sends the engagement projection 19 to the position adjacent to the engagement recess 11 as illustrated in FIGS. 8(a) and 8(b). In such movement of the engagement projection 19, the guide projection 22 of the movable head portion 21 is separated from the pressing escape hole 7 and, particularly, the inclined surface 22a of the guide projection 22 is pressed downward by the pressing portion 6 as shown in FIGS. 2(a) to 3(b). Further, the guide projection 23 is separated from the receiving portion 9 and enters the guide groove 8, and the leaf spring portion 17 flexibly deforms downward against the elastic force of the leaf spring portion 17 so that the distal surface 21a becomes inclined upward. In this state, the guide projection 23 becomes engaged with the guide groove 8. After the movable rod 16 is released from gripping and the movable head portion 21 is maintained fixed without rotating relative to the holder 1 as illustrated in FIGS. 7(a) and 7(b), the elastic force of the leaf spring portion 17 causes the movable rod 16 to restore its original position, canceling the twisting force of the movable rod 16. Further, the engagement projection 19 automatically enters the engagement recess 11 and is thus prevented from moving in the longitudinal direction X. This locks the core member 13 in the projected state P. In this state, the engagement projection 19 is engaged with the engagement recess 11.

Serrations 2a are formed on the outer circumference of the front portion of the outer circumferential wall 2. The fingers contact the serrations 2a when a surgery is performed or the core member 13 is projected or retracted. A mounting projection 5a, which prevents rolling of the holder 1, is formed along the outer circumference of a rear end portion of the outer circumferential wall 2.

The length of the medical edged tool as a whole in the longitudinal direction X is set to approximately 142 mm in the projected state P illustrated in FIGS. 2(a) to 3(b). The length of the medical edged tool as a whole in the longitudinal direction X in the accommodated state Q illustrated in FIGS. 5(a) to 6(b) is set to approximately 145 mm. The height of the holder 1 in the up-and-down direction Z is set to approximately 9 mm. The height of the front opening 4 in the up-and-down direction Z, or the height of the range S in the up-and-down direction Z, is set to approximately 6.4 mm. The maximum movement distance of the movable head portion 21 in the longitudinal direction X is set to approximately 22 mm. The twisting angle of the movable rod 16 is set to 10 to 45 degrees, or, preferably, 15 to 30 degrees, with easy manipulation by the user and the twisting strength of the movable rod 16 taken into consideration. In the leaf spring portion 17 in the states illustrated in FIG. 1(a) and FIGS. 5(a) to 6(b), the length between the movable rod 16 and the movable head portion 21 in the longitudinal direction X is set to approximately 40 mm. The thickness in the vicinity of the movable head portion 21 in the up-and-down direction Z is set to approximately 1.0 mm. The thickness in the vicinity of the movable rod 16 in the up-and-down direction Z is set to approximately 1.4 mm. The width in the vicinity of the movable head portion 21 in the left-and-right direction Y is set to approximately 3.7 mm. The width in the vicinity of the movable rod 16 in the left-and-right direction Y is set to approximately 4.5 mm. In other words, the portion of the leaf spring portion 17 in the vicinity of the movable head portion 21 is thin with a smaller thickness and narrow with a smaller width. This makes it easy for the portion to be twisted in the circumferential direction R and flexibly deformed in the up-and-down direction Z.

As a result, the hand tool of the illustrated embodiment is suitable particularly as the medical edged tool with the bendable blade body 24. Specifically, the orientation N of the blade body 24 is changed between the accommodated state Q and the projected state P. The blade body 24 is thus easily accommodated. This decreases the size of the front opening 4 of the holder 1 and thus provides a compact holder 1. Also, such sizing saves wrapping material.

The illustrated embodiment may be modified as follows.

In the illustrated embodiment, the brims 19a each serving as a stopper portion are formed at both of the front and rear end portions of the engagement projection 19 as illustrated in FIG. 11(a). However, the brim 19a may be provided only in one of the front and rear end portions of the engagement projection 19. With reference to FIG. 11b, extended stopper portions 19a, 11a, 12a may be formed at both front and rear end portions of the engagement projection 19 and both front and rear end portions of each engagement recess 11, 12. As illustrated in FIG. 11(c), stopper portions 11a, 12a each having a stepped shape may be provided at both front and rear end portions of each engagement recess 11, 12. With reference to FIG. 11(d), the stopper portions may be omitted from both the engagement projection 19 and the engagement recesses 11, 12. Alternatively, although not illustrated, three or more engagement recesses 11, 12 may be formed along the guide hole 10.

Figure 12:
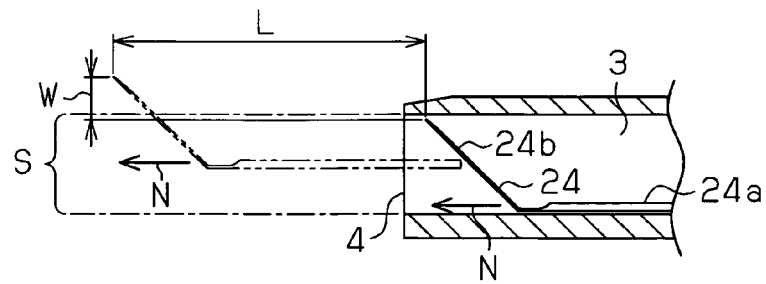
FIG. 12(a) is a cross-sectional view schematically showing a portion of a blade body of a modification held in an accommodated state.
FIG. 12(b) is a cross-sectional view schematically showing a portion of the blade body held in a projected state.
Figure 12:
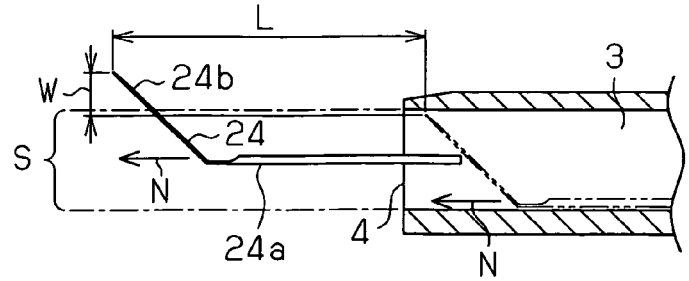

As illustrated in FIGS. 12(a) and 12(b), the blade body 24 may be translated without changing the orientation N between the accommodated state and the projected state. In this state, the position of the blade body 24 in the accommodated state and the position of the blade body 24 in the projected state is changed by the distance L in the longitudinal direction X of the holder 1 and by the distance W in the up-and-down direction Z of the holder 1 perpendicular to the longitudinal direction X. Although not illustrated, the position of the blade body 24 in the accommodated state and the position of the blade body 24 in the projected state may be changed by the distance W in the left-and-right direction Y of the holder 1 perpendicular to the longitudinal direction X.

In the blade body 24, the bending angle of the blade plate portion 24b with respect to the support plate portion 24a is set to approximately 45 degrees. However, the bending angle may be set to an angle other than approximately 45 degrees. The bending portion may have a curved shape or a plurality of bending portions may be provided. Such modifications may be made also in a case in which a component other than the blade body 24 is employed as the functional portion.

Various suitable structures may be employed as the guiding/restricting portion instead of the guide projections 22, 23 of the movable head portion 21, the pressing portion 6, the pressing escape hole 7, the guide groove 8, and the receiving portion 9 of the holder 1.

The movable head portion 21 and the leaf spring portion 17 may be provided separately and secured to each other. Alternatively, the leaf spring portion 17 and the movable rod 16 may be provided separately and secured to each other.

Various suitable mechanisms other than the mechanism of the illustrated embodiment may be employed as the movement mechanism of the movable rod 16 depending on the purpose and the form of the movable rod 16. The mechanisms include, for example, a knocking type mechanism generally used in a writing instrument such as a ballpoint pen and a screw type mechanism that causes the movable rod 16 to rotate and move in the longitudinal direction like a micrometer.

The present invention may be used in any suitable hand tool other than the medical edged tool such as a surgical edged tool. For example, the present invention may be used ballpoint pens, shavers, box cutters, knives, edged tools like chisels, earpicks, forks, cosmetic brushes, and lipsticks. Various suitable components may be employed as the functional portion depending on the type of the hand tools.

The invention claimed is:

1. A hand tool having a holder and a movable head portion to which a functional portion is secured, wherein the movable head portion is supported by the holder in a manner movable relative to the holder between an accommodated state, in which the movable head portion is accommodated in the holder together with the functional portion, and a projected state, in which the functional portion is projected from the holder, wherein the orientation of the functional portion in the accommodated state and the orientation of the functional portion in the projected state are different from each other, wherein the hand tool further comprises a manipulation body that supports the movable head portion, wherein the manipulation body allows the movable head portion to move between the accommodated state and the projected state, the manipulation body includes an elastic body that applies an elastic force to the movable head portion between the accommodated state and the projected state, wherein the elastic body causes the movable head portion to incline, and the movable head portion is accommodated in the holder by the elastic force of the elastic body, wherein the movable head portion projects the functional portion from the holder against the elastic force of the elastic body.

2. The hand tool according to claim 1, wherein the position of the functional portion in the accommodated state and the position of the functional portion in the projected state are different in a longitudinal direction of the holder and in a direction perpendicular to the longitudinal direction.

3. The hand tool according to claim 1, wherein the holder and the movable head portion include a guiding/restricting portion that guides the movable head portion in a manner movable relative to the holder between the accommodated state and the projected state and allows the movable head portion to incline.

4. The hand tool according to claim 3, wherein the guiding/restricting portion of the movable head portion is a guide projection, wherein the guiding/restricting portion of the holder includes a pressing portion that presses and contacts the guide projection of the movable head portion and an escape portion that releases the guide projection from pressing and contacting.

5. The hand tool according to claim 1, wherein the manipulation body further includes a manipulating portion having a finger support portion, wherein the elastic body is arranged between the manipulating portion and the movable head portion, and wherein the movable head portion is supported by the elastic body.

6. The hand tool according to claim 5, wherein the manipulating portion and the elastic body of the manipulation body are formed integrally with the movable head portion.

* * * * *